(12) United States Patent
Hersch et al.

(10) Patent No.: US 7,501,283 B2
(45) Date of Patent: Mar. 10, 2009

(54) FLUID DISPENSING APPARATUS

(75) Inventors: Michael Hersch, Redondo Beach, CA (US); Henry Palermo, Anaheim Hills, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 183 days.

(21) Appl. No.: 10/639,021

(22) Filed: Aug. 11, 2003

(65) Prior Publication Data

US 2005/0035156 A1 Feb. 17, 2005

(51) Int. Cl.
*G01N 35/00* (2006.01)

(52) U.S. Cl. .................. 436/46; 422/63; 422/100; 436/180; 222/144

(58) Field of Classification Search .............. 222/144, 222/325, 181.3, 420, 108; 422/63, 100; 436/46, 436/180
See application file for complete search history.

(56) References Cited

U.S. PATENT DOCUMENTS

| | | | |
|---|---|---|---|
| 2,709,025 A | 5/1955 | Scott | |
| 3,294,290 A | 12/1966 | Erickson et al. | |
| 3,904,079 A * | 9/1975 | Kross | 222/2 |
| 4,018,363 A | 4/1977 | Cassia | |
| 4,039,775 A | 8/1977 | Andra | |
| 4,099,483 A | 7/1978 | Henderson | |
| 4,149,633 A | 4/1979 | Nilson | |
| 4,199,558 A | 4/1980 | Henderson | |
| 4,258,759 A * | 3/1981 | Achen | 141/100 |
| 4,356,727 A | 11/1982 | Brown et al. | |
| 4,604,964 A | 8/1986 | Gordon et al. | |
| 4,678,752 A | 7/1987 | Thorne et al. | |
| 4,731,335 A | 3/1988 | Brigati | |
| 4,741,898 A | 5/1988 | Mallik et al. | |
| 4,764,342 A | 8/1988 | Kelln et al. | |
| 4,798,311 A | 1/1989 | Workum | |
| 4,801,431 A | 1/1989 | Cuomo et al. | |
| 4,834,019 A | 5/1989 | Gordon et al. | |
| 4,846,636 A | 7/1989 | Danby et al. | |
| 4,867,347 A | 9/1989 | Wass et al. | |
| 4,886,192 A | 12/1989 | Cassia | |

(Continued)

FOREIGN PATENT DOCUMENTS

EP 0185330 6/1986

(Continued)

OTHER PUBLICATIONS

European Search Report for EP Appln No. 06101495.7, mailed Dec. 18, 2006 (10 pages).

(Continued)

*Primary Examiner*—James F Hook
(74) *Attorney, Agent, or Firm*—Blakely, Sokoloff, Taylor & Zafman, LLP

(57) ABSTRACT

A fluid dispensing apparatus includes a mounting assembly having a plurality of mounting apertures and a plurality of fluid dispensing cartridges positioned within the mounting apertures. The mounting apertures and cartridges include matching cross-sectional profiles that lack symmetry. Each fluid dispensing cartridge includes a fluid reservoir, at least one valve, a metering chamber and a piston. The apparatus also includes a magnetic switch assembly controlling the movement of the piston and a means for damping the movement of the piston.

35 Claims, 8 Drawing Sheets

U.S. PATENT DOCUMENTS

| | | | |
|---|---|---|---|
| 4,921,136 A | 5/1990 | Roggenburg, Jr. |
| 4,927,061 A | 5/1990 | Leigh et al. |
| 4,946,076 A | 8/1990 | Hackmann et al. |
| 4,955,512 A | 9/1990 | Sharples |
| 4,961,508 A | 10/1990 | Weimer et al. |
| 4,969,581 A | 11/1990 | Seifert et al. |
| 4,972,978 A | 11/1990 | DeLuca |
| 4,974,754 A | 12/1990 | Wirz |
| 4,978,036 A | 12/1990 | Burd |
| 4,985,206 A | 1/1991 | Bowman et al. |
| 5,002,736 A | 3/1991 | Babbitt et al. |
| 5,033,656 A | 7/1991 | Blette et al. |
| 5,035,350 A | 7/1991 | Blette et al. |
| 5,068,091 A | 11/1991 | Toya |
| 5,225,325 A | 7/1993 | Miller et al. |
| 5,232,664 A | 8/1993 | Krawzak et al. |
| 5,242,083 A | 9/1993 | Christine et al. |
| 5,244,787 A | 9/1993 | Key et al. |
| 5,275,309 A | 1/1994 | Baron et al. |
| 5,316,452 A | 5/1994 | Bogen et al. |
| 5,322,771 A | 6/1994 | Rybski et al. |
| 5,338,358 A | 8/1994 | Mizusawa et al. |
| 5,355,439 A | 10/1994 | Bernstein et al. |
| 5,356,039 A | 10/1994 | Christine et al. |
| 5,418,138 A | 5/1995 | Miller et al. |
| 5,424,036 A | 6/1995 | Ushikubo |
| 5,433,351 A | 7/1995 | Okuyama et al. |
| 5,439,649 A | 8/1995 | Tseung et al. |
| 5,578,452 A | 11/1996 | Shi et al. |
| 5,580,523 A | 12/1996 | Bard |
| 5,595,707 A | 1/1997 | Copeland et al. |
| 5,609,822 A | 3/1997 | Carey et al. |
| 5,626,262 A | 5/1997 | Fitten et al. |
| 5,645,114 A | 7/1997 | Bogen et al. |
| 5,650,327 A | 7/1997 | Copeland et al. |
| 5,654,200 A | 8/1997 | Copeland et al. |
| 5,675,715 A | 10/1997 | Bernstein et al. |
| 5,810,204 A | 9/1998 | Devlin et al. |
| 5,839,091 A | 11/1998 | Rhett et al. |
| 5,843,700 A | 12/1998 | Kerrod et al. |
| 5,846,396 A | 12/1998 | Zanzucchi et al. |
| 5,855,302 A | 1/1999 | Fisscher |
| 5,857,595 A | 1/1999 | Nilson |
| 5,947,167 A | 9/1999 | Bogen et al. |
| 5,948,359 A | 9/1999 | Kalra et al. |
| 5,950,874 A * | 9/1999 | Sindoni ................. 222/144.5 |
| 5,954,167 A | 9/1999 | Richardson et al. |
| 5,964,454 A | 10/1999 | Volpel |
| 5,971,223 A | 10/1999 | Fisscher |
| 6,001,309 A * | 12/1999 | Gamble et al. .............. 422/100 |
| 6,045,759 A | 4/2000 | Ford et al. |
| 6,076,583 A | 6/2000 | Edwards |
| 6,092,695 A | 7/2000 | Loeffler |
| 6,093,574 A | 7/2000 | Druyor-Sanchez et al. |
| 6,096,271 A | 8/2000 | Bogen et al. |
| 6,180,061 B1 | 1/2001 | Bogen et al. |
| 6,183,693 B1 | 2/2001 | Bogen et al. |
| 6,192,945 B1 | 2/2001 | Ford et al. |
| 6,216,916 B1 | 4/2001 | Maddox et al. |
| 6,238,910 B1 | 5/2001 | Custance et al. |
| 6,244,474 B1 | 6/2001 | Loeffler |
| 6,273,298 B1 * | 8/2001 | Post ........................ 222/105 |
| 6,296,809 B1 | 10/2001 | Richards et al. |
| 6,335,166 B1 * | 1/2002 | Ammann et al. ................ 435/6 |
| 6,343,716 B1 | 2/2002 | Baudin et al. |
| 6,349,264 B1 | 2/2002 | Rhett et al. |
| 6,352,861 B1 | 3/2002 | Copeland et al. |
| 6,387,326 B1 | 5/2002 | Edwards et al. |
| 6,415,961 B2 | 7/2002 | Bonningue |
| 6,416,713 B1 | 7/2002 | Ford et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,516,620 B2 | 2/2003 | Lang |
| 6,541,261 B1 | 4/2003 | Bogen et al. |
| 6,543,652 B1 | 4/2003 | Kelder et al. |
| 6,544,798 B1 | 4/2003 | Christensen et al. |
| 6,580,056 B1 | 6/2003 | Tacha |
| 6,582,962 B1 | 6/2003 | Richards et al. |
| 6,594,537 B1 | 7/2003 | Bernstein et al. |
| 6,605,213 B1 * | 8/2003 | Ammann et al. ............ 210/222 |
| 6,632,598 B1 | 10/2003 | Zhang et al. |
| 6,635,225 B1 | 10/2003 | Thiem et al. |
| 6,673,620 B1 | 1/2004 | Loeffler et al. |
| 6,735,531 B2 | 5/2004 | Rhett et al. |
| 6,746,851 B1 | 6/2004 | Tseung et al. |
| 6,758,360 B2 | 7/2004 | Van Giezen et al. |
| 6,783,733 B2 | 8/2004 | Bogen et al. |
| 6,827,900 B2 | 12/2004 | Thiem et al. |
| 6,827,901 B2 | 12/2004 | Copeland et al. |
| 6,855,552 B2 | 2/2005 | Towne et al. |
| 6,855,559 B1 | 2/2005 | Christensen et al. |
| 6,899,283 B2 * | 5/2005 | Ohnishi et al. ........... 239/102.1 |
| 6,943,029 B2 | 9/2005 | Copeland et al. |
| 6,945,128 B2 | 9/2005 | Ford et al. |
| 6,991,934 B2 | 1/2006 | Walton et al. |
| 6,998,270 B2 | 2/2006 | Tseung et al. |
| 7,007,824 B2 | 3/2006 | Danby et al. |
| 7,070,951 B2 | 7/2006 | Zhang et al. |
| 7,118,918 B2 | 10/2006 | Copeland et al. |
| 7,217,392 B2 | 5/2007 | Bogen et al. |
| 7,220,589 B2 | 5/2007 | Richards et al. |
| 7,270,785 B1 | 9/2007 | Lemme et al. |
| 2001/0044603 A1 | 11/2001 | Harrold |
| 2002/0079318 A1 | 6/2002 | Wurzinger |
| 2002/0114733 A1 | 8/2002 | Copeland et al. |
| 2003/0100043 A1 | 5/2003 | Kalra et al. |
| 2003/0157545 A1 | 8/2003 | Jevons et al. |
| 2003/0203493 A1 | 10/2003 | Lemme et al. |
| 2004/0033163 A1 | 2/2004 | Tseung et al. |
| 2004/0091395 A1 | 5/2004 | Ward et al. |
| 2004/0120862 A1 | 6/2004 | Lang et al. |
| 2004/0191128 A1 | 9/2004 | Bogen et al. |
| 2004/0197230 A1 | 10/2004 | Lemme et al. |
| 2004/0266015 A1 | 12/2004 | Favuzzi et al. |
| 2005/0035156 A1 | 2/2005 | Hersch et al. |
| 2005/0064535 A1 | 3/2005 | Favuzzi et al. |
| 2005/0135972 A1 | 6/2005 | Lemme et al. |
| 2005/0153453 A1 | 7/2005 | Copeland et al. |
| 2005/0164374 A1 | 7/2005 | Kram |
| 2005/0191214 A1 | 9/2005 | Tseung et al. |
| 2005/0281711 A1 | 12/2005 | Testa et al. |
| 2006/0019332 A1 | 1/2006 | Zhang et al. |
| 2006/0040341 A1 | 2/2006 | Bland et al. |
| 2006/0045806 A1 | 3/2006 | Winther et al. |
| 2006/0063265 A1 | 3/2006 | Welcher et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0120921 A1 | 6/2006 | Elliot et al. |
| 2006/0134793 A1 | 6/2006 | Key et al. |
| 2006/0147351 A1 | 7/2006 | Falb et al. |
| 2006/0190185 A1 | 8/2006 | Ford et al. |
| 2006/0191952 A1 | 8/2006 | Kalra et al. |
| 2006/0252025 A1 | 11/2006 | Nitta et al. |
| 2006/0263268 A9 | 11/2006 | Tseung et al. |
| 2006/0265133 A1 | 11/2006 | Cocks et al. |
| 2007/0038491 A1 | 2/2007 | Samuhel et al. |

FOREIGN PATENT DOCUMENTS

| | | |
|---|---|---|
| EP | 0557871 | 9/1993 |
| EP | 1028320 | 8/2000 |
| GB | 2037255 | 7/1980 |

| | | |
|---|---|---|
| JP | 6-510860 | 12/1994 |
| JP | 2001-512823 | 8/2001 |
| JP | 2001-522033 | 11/2001 |
| WO | WO 95/08774 | 3/1995 |
| WO | WO 99/08090 | 2/1999 |
| WO | WO 99/022867 | 5/1999 |
| WO | WO 00/12994 | 3/2000 |
| WO | WO 01/041918 | 6/2001 |
| WO | WO 02/072264 | 9/2002 |
| WO | WO 03/091710 | 11/2003 |
| WO | WO 03/106033 | 12/2003 |
| WO | WO 2004/059288 | 7/2004 |
| WO | WO 2004/074847 | 9/2004 |
| WO | WO 2005/000731 | 1/2005 |

OTHER PUBLICATIONS

European Search Report for EP Appln No. 06101497.3, mailed Jun. 20, 2006 (6 pages).

European Search Report for EP Appln No. 06101498.1, mailed Jun. 20, 2006 (6 pages).

Zhang, Guangrong, et al., "Deparaffinization compositions and methods for their use," Reissue U.S. Appl. No. 11/250,142, filed Oct. 13, 2005.

Shi, Shan-Rong, et al., "Enhancement of immunochemical staining in aldehyde-fixed tissue," Reissue U.S. Appl. No. 11/249,180, filed Oct. 11, 2005.

Office Action for Japanese Application No. 2006-523317 dated Nov. 30, 2007 (9 pages).

PCT Search Report for PCT Appln No. PCT/US2007/012400, mailed Nov. 16, 2007 (13 pages).

* cited by examiner

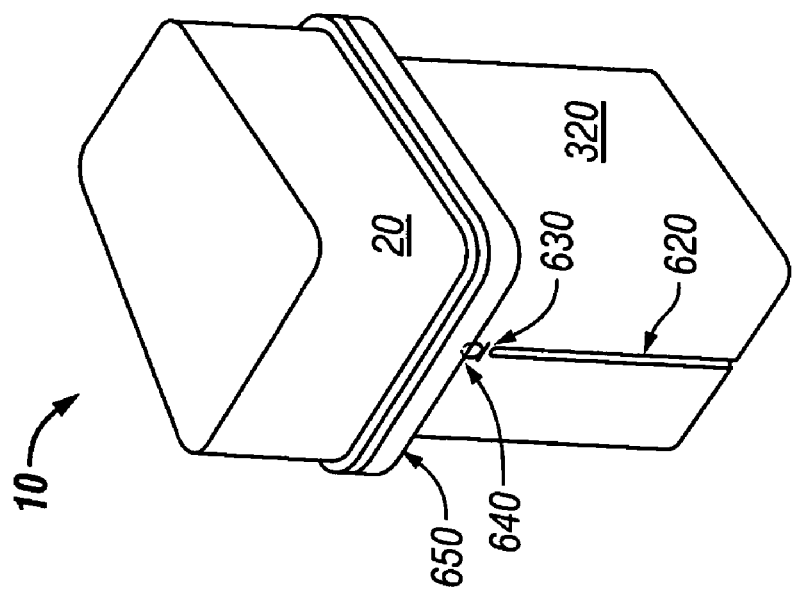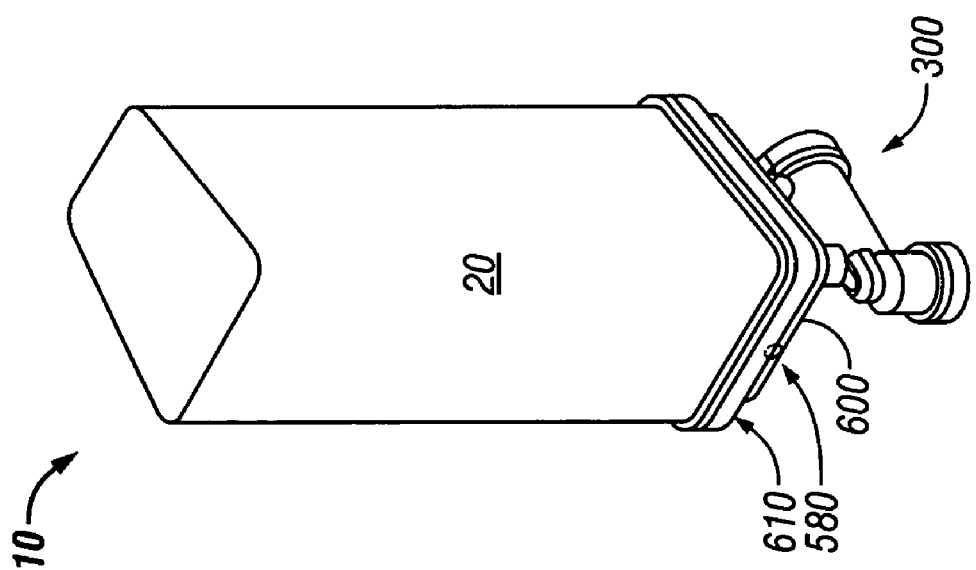

FLUID DISPENSING APPARATUS

FIELD OF THE INVENTION

The present invention relates to medical laboratory fluid dispensing devices and related systems.

BACKGROUND OF THE INVENTION

While conducting biological tests, it often is necessary to dispense liquids such as reagents onto test slides containing tissue specimens. When analyzing tumor tissue for example, a thinly sliced section of the tissue might be placed on a slide and processed through a variety of steps, including dispensing predetermined amounts of liquid reagents onto the tissue. Automated reagent fluid dispensing devices have been developed to precisely apply a sequence of preselected reagents to test slides.

One example of a known reagent dispensing system is illustrated in U.S. Pat. No. 5,232,664. In this system, a reagent dispensing tray can receive plural reagent containers and may include a means for positioning selected reagent containers over slides to receive reagent. An air cylinder or equivalent actuator makes contact with an individual cartridge effecting movement of a spring loaded displacement member, which in turn causes reagent fluid to be applied over the slides.

One disadvantage associated with conventional reagent dispensing systems (such as disclosed in U.S. Pat. No. 5,232,664) concerns the use of a contact actuator assembly to control the dispensing of reagent. Systems that include a contact actuator assembly require precise mounting and rotational positioning of the actuator assembly with respect to the cartridges. In view of this disadvantage, there exists a need for a reagent dispensing system including a non-contact actuator assembly that does not require precise mounting and rotational positioning with respect to the cartridges.

A further disadvantage associated with conventional reagent dispensing systems involves uncontrolled or erratic dispensing of reagent fluid caused by the unchecked movement of the spring loaded displacement member or piston. In view of this disadvantage, there exists a need for a reagent dispensing system including a damping system that slows the movement of the piston and prevents uncontrolled or erratic dispensing of reagent fluid.

An additional disadvantage associated with conventional reagent dispensing systems concerns the potential misalignment of individual cartridges within mounting apertures of a mounting assembly. In view of this disadvantage, there exists a need for a reagent dispensing system including cartridges that are shaped so as to self-align within similarly-shaped mounting apertures.

SUMMARY OF THE INVENTION

The present invention alleviates to a great extent the above-noted and other disadvantages of known fluid dispensing apparatus by providing a fluid dispensing cartridge that can dispense small amounts of fluids accurately and optionally operates in conjunction with an associated fluid dispensing system that operates plural fluid dispensing cartridges.

One aspect of the present invention involves a fluid dispensing cartridge that includes a fluid reservoir, a dispensing assembly and a mounting assembly. In one embodiment, the dispensing assembly includes metering components such as a first valve assembly, a second valve assembly and a metering chamber between them. An actuator assembly operates with the metering components to meter a desired volume of fluid from the fluid reservoir into the metering chamber, and then to expel the metered fluid from the metering chamber out of the cartridge, such as on a desired target such as a fluid bath or a slide.

In one embodiment, the metering components operate in conjunction with an external switch, such as a solenoid or electromagnet operated switch including a permanent magnet for displacing a spring loaded displacement member (also referred to as a "piston") within the fluid dispensing cartridge, creating a pressure gradient within the metering chamber. The pressure differential created between the metering chamber and the fluid reservoir assists with opening the first valve allowing fluid flow into the chamber. As the displacement member is released it returns to its resting position forcing the fluid out of the dispensing chamber into and out of the dispensing cartridge via the second valve. Optionally the dispensing assembly includes a damping system such as including a bleed passageway between the fluid reservoir and the spring loaded displacement member.

The displacement member or piston is preferably is made of a magnetically attractive material. The magnetic attraction of the displacement member with the switch is selected to be sufficiently high to overcome the spring bias in the opposite direction. This attraction moves the piston in an anterior direction creating a pressure differential between the metering chamber and fluid reservoir, such that the first valve opens and the fluid in the reservoir enters the metering chamber. When the solenoid or electromagnet is de-energized, the piston returns to the first position, as impelled by the spring load. During the return movement of the piston, fluid is pushed out of the metering chamber through the second valve. Of course alternate embodiments are possible, such as for example dual solenoid or electromagnet assemblies disposed on the anterior and posterior ends of the piston.

A further aspect of the present invention involves a fluid damping system for dampening the motion of the piston. The fluid damping system may include a bleed passageway communicating between the anterior of the piston and the fluid chamber, that helps prevent potential erratic dispensing of fluid by slowing the motion of the piston. A further advantage of the bleed passageway is that it equalizes pressure changes in the fluid reservoir. An increase in fluid reservoir pressure may be caused, for example, by an increase in atmospheric pressure or by compression of the cartridge. Without the bleed passageway, an increase in fluid reservoir pressure could push the piston away from its seat causing fluid to be dispensed inadvertently.

The fluid dispensing cartridge of the present invention optionally may be used with a fluid dispensing apparatus including a plurality of stations at which fluid dispensing cartridges optionally are located. The stations preferably include mounting apertures that are shaped to receive the cartridges adjacent to a corresponding external actuating switch apparatus. Although the cartridges may rely on gravitational force to seat within their respective mounting apertures, optionally the cartridges are releasably attached to the fluid dispensing apparatus using a mounting assembly. One example of a mounting assembly includes a ball detent slot located on each cartridge and a corresponding passive or spring loaded ball located within the mounting aperture on the fluid dispensing apparatus. Of course it should be appreciated that any other form of mounting assembly may be used that can retain the fluid dispensing cartridge in a desired physical relation to its respective external switch assembly. Each mounting mechanism optionally also includes a ball detent step and a ball detent seat adjacent to the ball detent slot, wherein each ball detent seat is dimensioned to releasably hold a corresponding ball.

An additional aspect of the present invention involves a fluid dispensing apparatus including mounting apertures shaped so as to self-align similarly shaped cartridges, wherein the cartridges and openings have matching cross-sectional profiles. In one embodiment, the cartridges and mounting apertures include matching cross-sectional profiles that lack symmetry. By way of example, the cross-sectional profiles may be trapezoidal or wedge-shaped.

These and other features and advantages of the present invention will be appreciated from review of the following detailed description of the invention, along with the accompanying figures in which like reference numerals refer to like parts throughout.

BRIEF DESCRIPTION OF THE DRAWINGS

FIG. 7 is a perspective view of an embodiment of an assembly in accordance with the present invention;

FIG. 8 is a perspective view of an embodiment of an assembly in accordance with the present invention.

DETAILED DESCRIPTION OF THE INVENTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Figure 1:
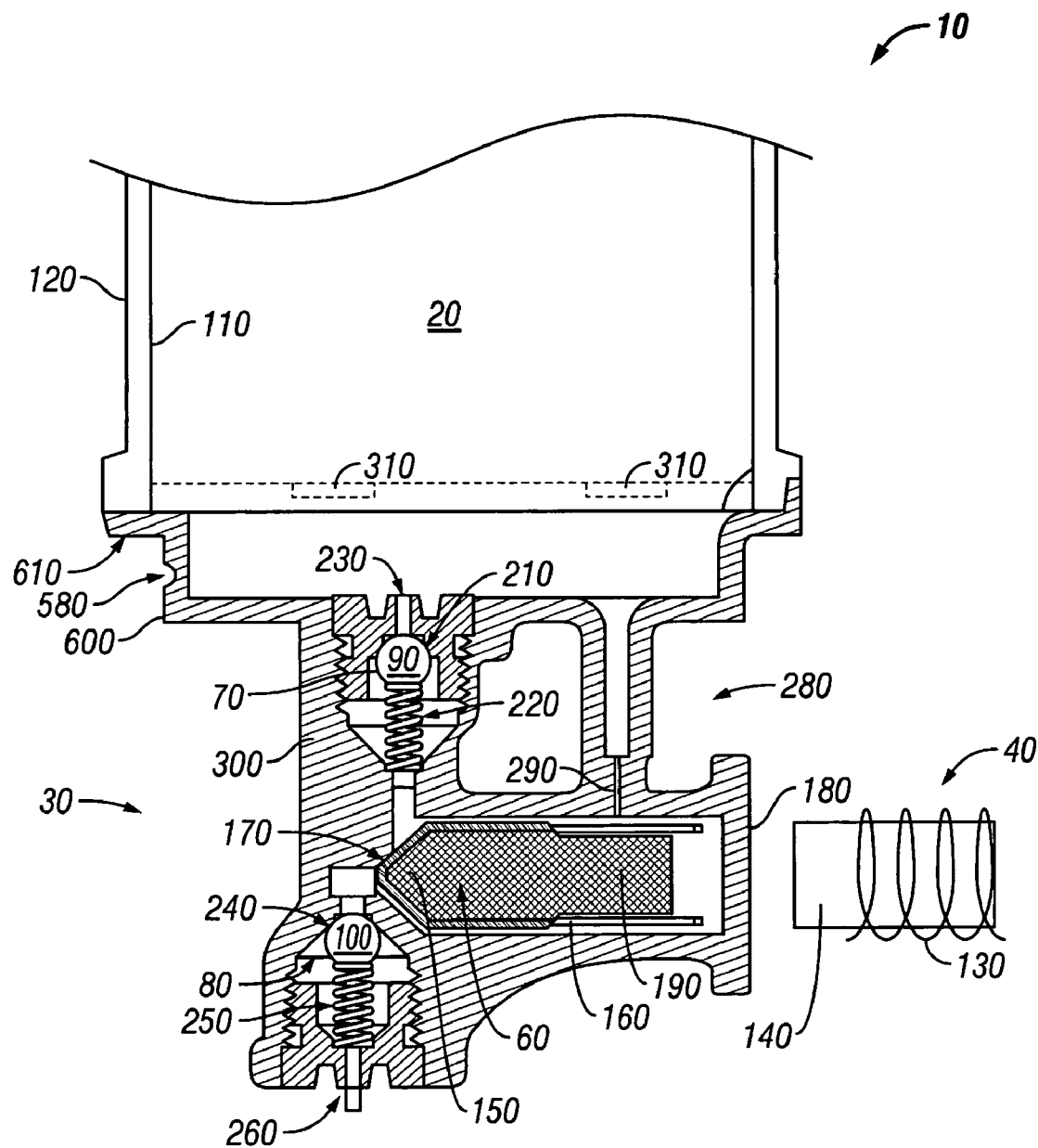
FIG. 1 is a cross-sectional view of an embodiment of an assembly in accordance with the present invention.
Figure 2:
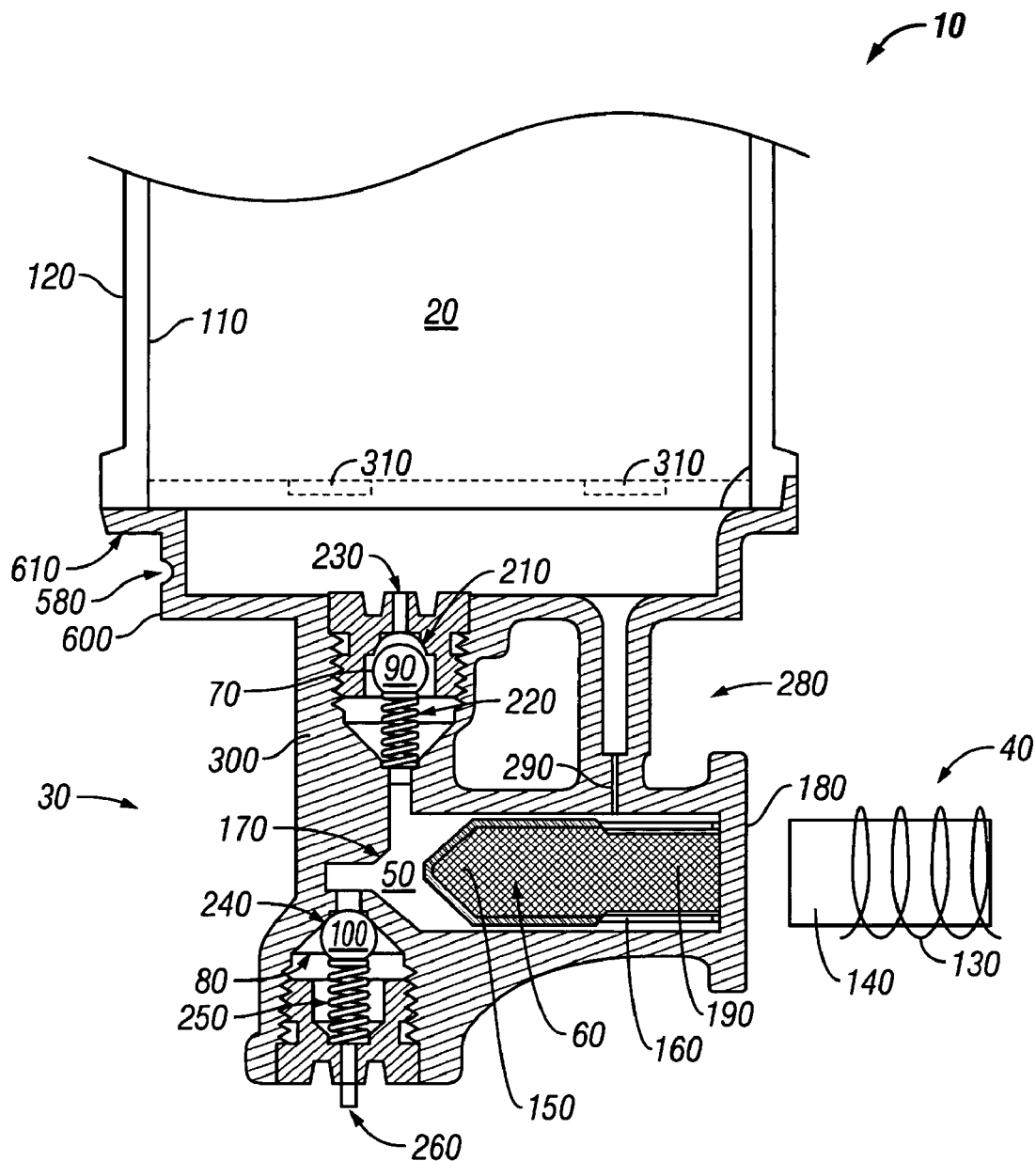
FIG. 2 is a cross-sectional view of an embodiment of an assembly in accordance with the present invention.
Figure 3:
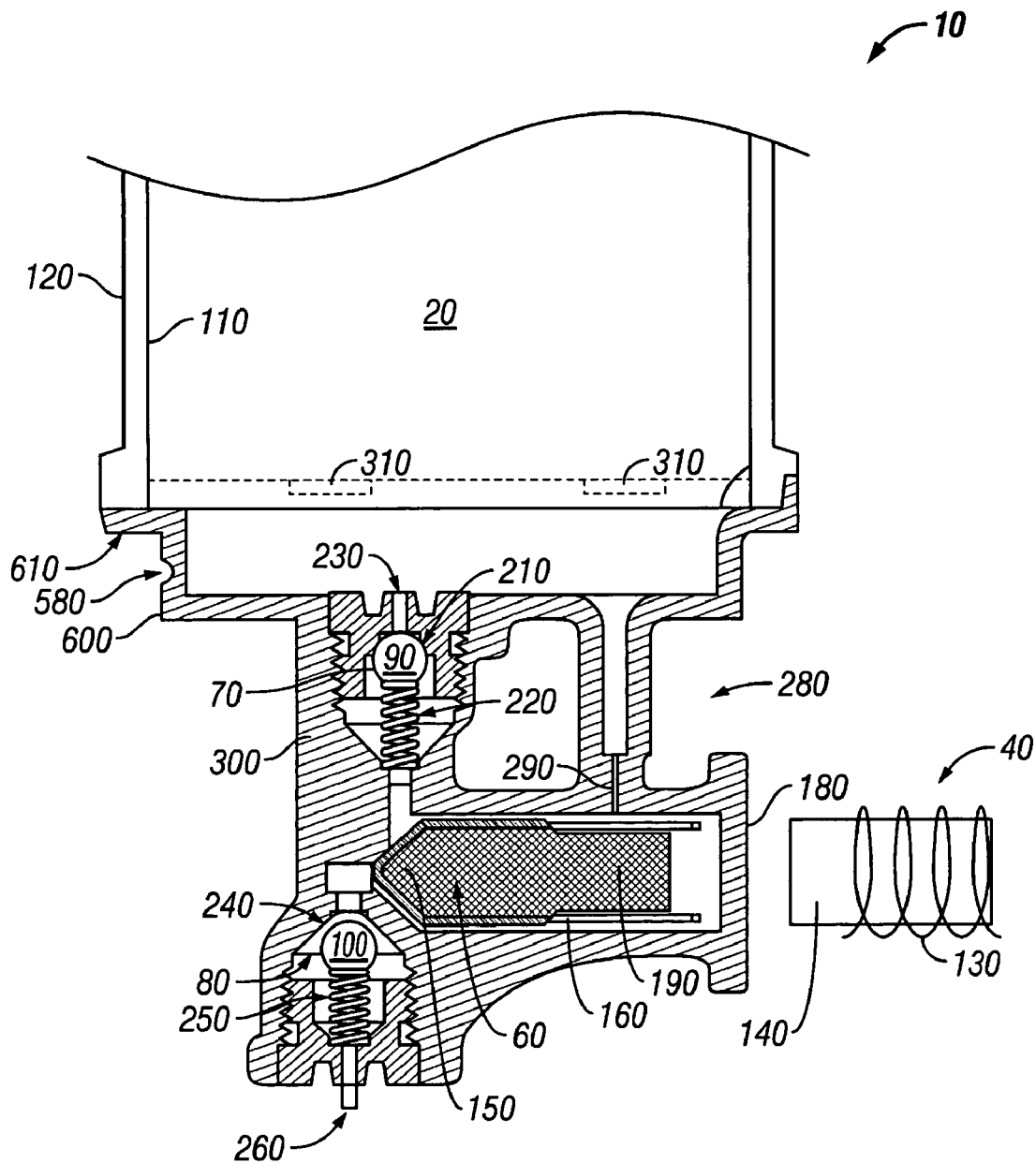
FIG. 3 is a cross-sectional view of an embodiment of an assembly in accordance with the present invention.

FIGS. 1-3 show a preferred embodiment of a fluid dispensing cartridge 10 in accordance with the present invention. The fluid dispensing cartridge 10 includes a fluid reservoir 20, a fluid dispensing assembly 30 in communication with the fluid reservoir 20 and an actuator assembly 40. The fluid dispensing assembly 30 includes a fluid metering chamber 50, a piston 60 and a valve assembly 70,80. Optionally the valve assembly includes first 70 and second 80 one-way ball valves, such as including spring loaded balls 90,100. The first and second valves 70,80 optionally may be one-way ball valves, such as including spring loaded balls 90,100.

According to a preferred embodiment, fluid reservoir 20 includes a collapsible liner 110, optionally a replaceable fluid bladder. It should be appreciated that the liner or bladder 110 may be made of any suitable material that is substantially fluid impermeable and is flexible, such as polyethylene or polypropylene. Moreover, use of a collapsible liner or bladder 110 assists with reducing ambient air contamination, extending the shelf life of the fluid contained in it. In an embodiment in which a collapsible liner or bladder 110 is used, it is preferred to include a substantially rigid cover 120 that supports the liner or bladder 110, and also can provides a grasping surface for handling, and a marking surface as well. According to other embodiments, fluid reservoir 20 does not include a fluid bladder such that the fluid is contained solely within the substantially rigid cover 120. Rigid cover 120 preferably includes a conventional one-way check valve to stabilize the pressure within the fluid reservoir 20 by allowing air to be sucked in as fluid exits.

In a preferred embodiment, the actuating assembly 40 includes an external switch, such as a magnetic switch including a coil 130 and a permanent magnet 140 to attract and thereby displace the piston 60 as desired. Advantageously, the use of a non-contact actuating assembly such as an external switch lessens the need to precisely mount and rotationally position the actuator assembly 40 with respect to the cartridge 10. Piston 60 preferably comprises a magnetic material attracted to the permanent magnet 140 when actuated. Optionally, the piston 60 includes a metallic core that is coated with a relatively non-corroding layer. By way of example, the piston 60 may include an iron or steel core coated in Teflon®. The piston 60 preferably is spring loaded, biased in a direction away from the magnetic switch, i.e. towards the posterior end 150 of the piston 60.

In the illustrated embodiment, a piston spring 160 is provided to bias the piston 60 towards piston seat 170. When the coil 130 is energized, the resulting magnetic attraction between piston 60 and magnet 140 momentarily overcomes force of piston spring 160 causing the piston 60 to move in an anterior direction from a resting position against seat 170 (as seen in FIG. 1) to a displaced position against wall portion 180 (as seen in FIG. 2). When the coil 130 is de-energized, the piston 60 is returned to the original, resting position as impelled by the spring loading of piston spring 160. Of course alternate embodiments are possible, such as dual solenoids or electromagnets both on the posterior and anterior ends 150, 190 of the piston 60.

As shown in FIG. 2, the movement of the piston 60 away from seat 170 creates a negative pressure gradient within fluid metering chamber 50. The pressure differential between the metering chamber 50 and fluid reservoir works against valve spring 220 by pulling the valve ball 90 away from seat 210. When the valve ball 90 is pulled away from seat 210, the first valve 70 opens for a predetermined duration causing a predetermined amount of fluid to be metered from the fluid reservoir 20 into the metering chamber 50 via nozzle 230. The flow of fluid into the metering chamber 50 reduces the negative pressure differential causing valve ball 90 to be pushed back into seat 210.

As shown in FIG. 3, the return of piston 60 to the resting position creates a positive pressure gradient in the metering chamber 50. The increased pressure momentarily overcomes the force of valve spring 250 forcing valve ball 100 away from seat 240 such that the predetermined amount of fluid is dispensed through nozzle 260. The flow of fluid out of the metering chamber 50 reduces the pressure gradient, thereby closing the valve 80.

According to one aspect of the present invention, the fluid dispensing cartridge 10 includes a means 280 for damping the motion of the piston 60. The means 280 for damping optionally includes a bleed passageway 290 of predetermined diameter that is filled with solution slowing the motion of the piston 60 preventing erratic dispensing of fluid. The bleed passageway 290 is disposed between the fluid reservoir 20 and the anterior end 190 of the piston 60. The diameter of the bleed passageway 290 can be increased to decrease the amount of damping introduced by damping means 280. Conversely, decreasing the diameter of bleed passageway 290 can increase the amount of damping. Advantageously, the damping means 280 prevents the cartridge 10 from leaking fluid due to compression of the cartridge 10 or changes in atmospheric pressure by substantially equalizing the pressure at either end of the piston 60 despite pressure changes in the fluid reservoir.

Figure 4:
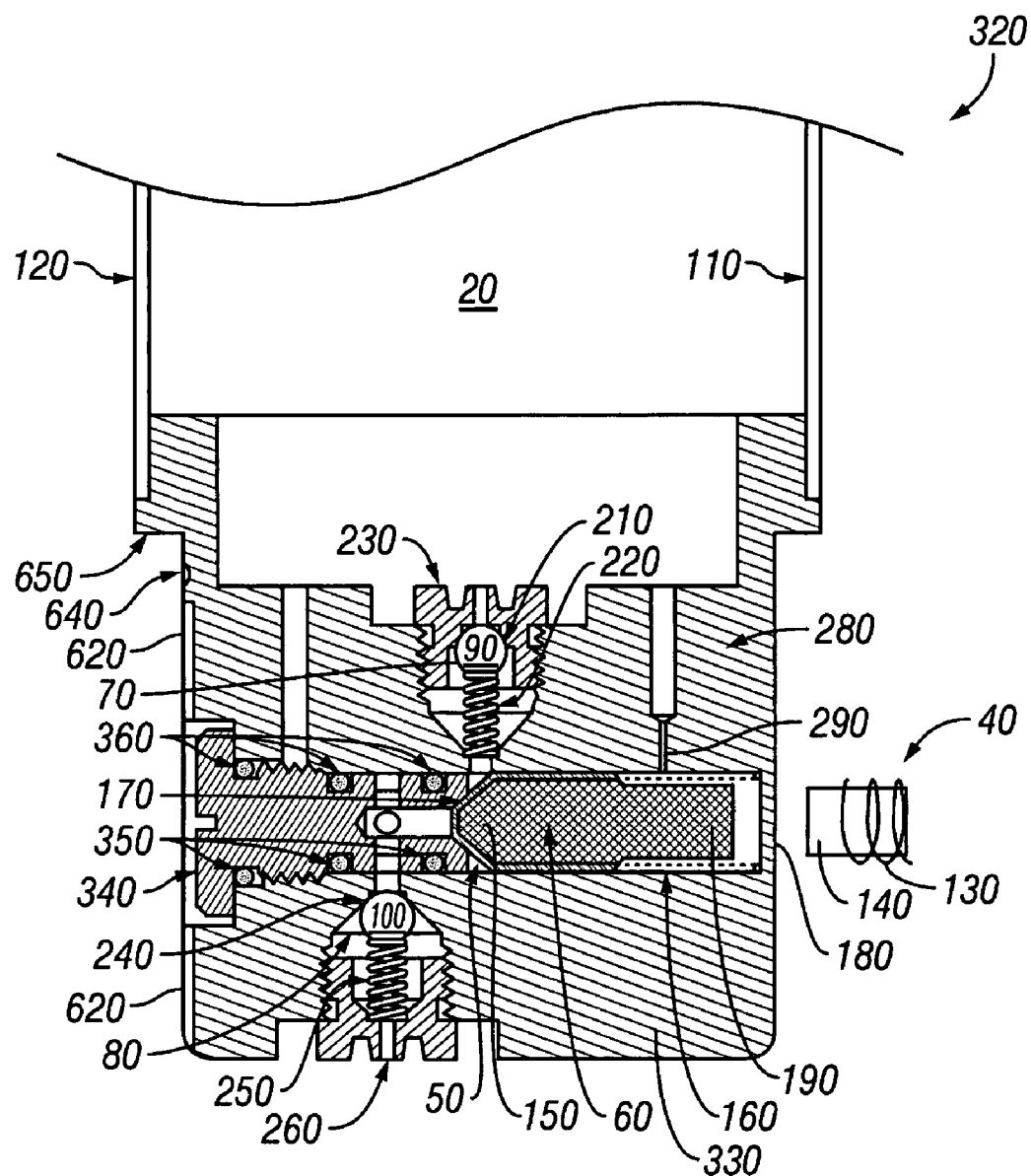
FIG. 4 is a cross-sectional view of an embodiment of an assembly in accordance with the present invention.

With further reference to FIGS. 1-3, the fluid dispensing assembly 30 is preferably disposed within a casing 300 shaped to fit the contour of the fluid dispensing assembly 30. Optionally, the casing 300 is releasably attached to the fluid reservoir 20 using tabs 310, or the like. As shown in FIG. 4, in an alternative embodiment wherein like elements of the embodiment of FIGS. 1-3 have been numbered accordingly, cartridge 320 includes fluid dispensing assembly 30 disposed within a housing 330 that does not follow the contours of the fluid dispensing assembly 20. The housing 330 optionally includes a removable plug 340 providing access to valves 70,80 and piston 60 in case they require repair or replacement. The plug 340 optionally includes grooves 350 for O-rings 360 to prevent fluid leakage.

Figure 5:
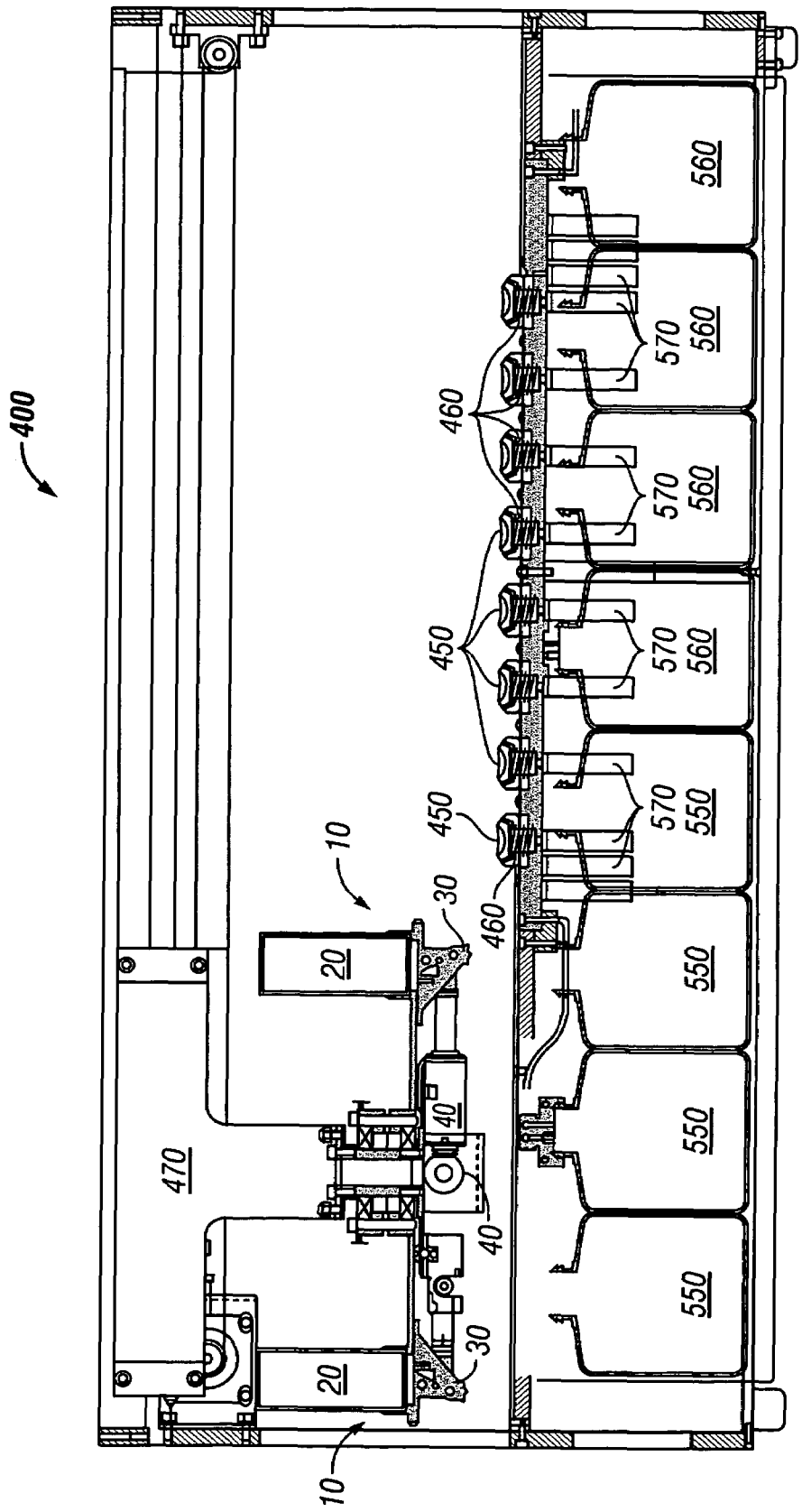
FIG. 5 is a front view of an embodiment of an assembly in accordance with the present invention.
Figure 6:
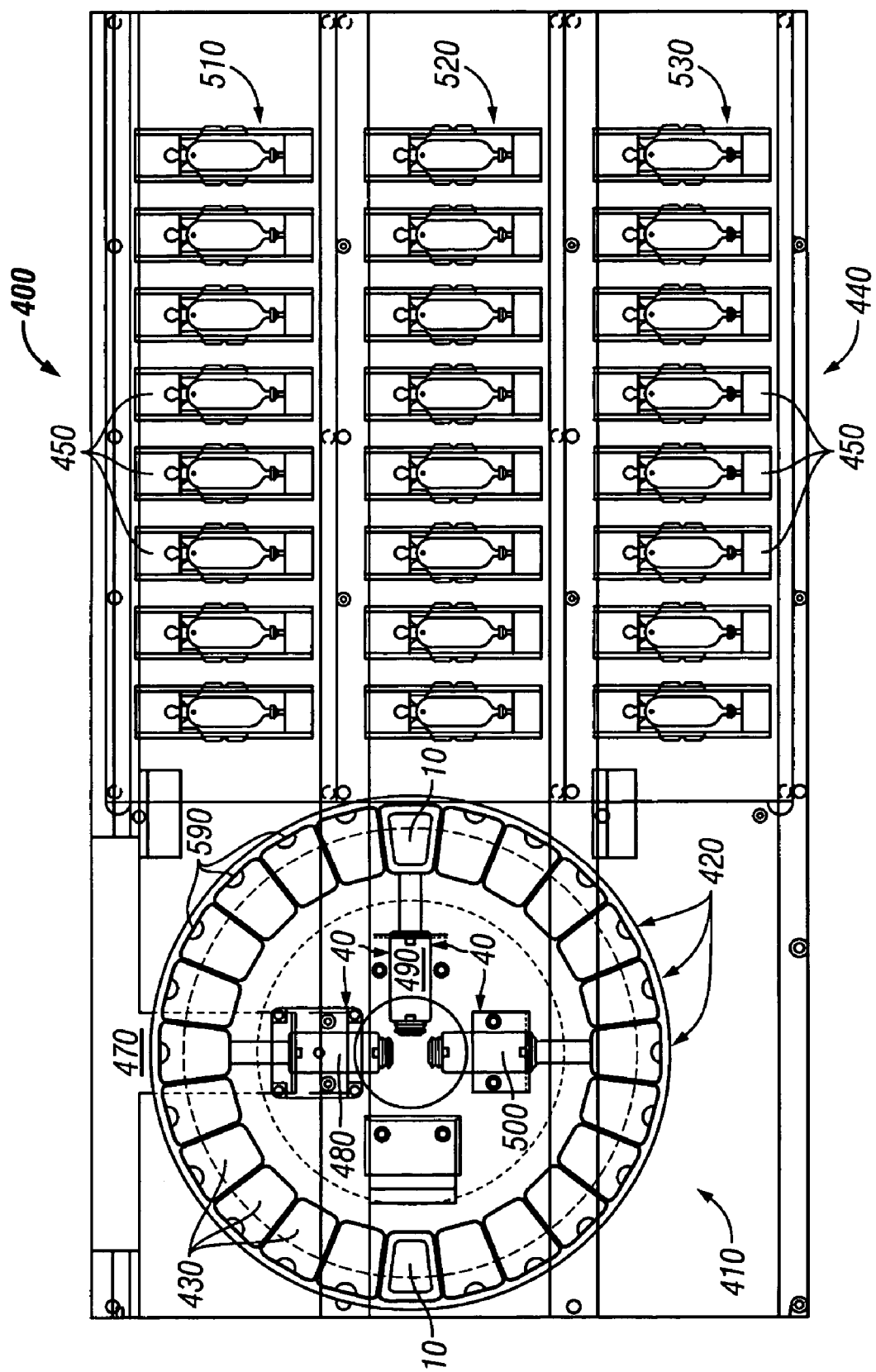
FIG. 6 is a top view of an embodiment of an assembly in accordance with the present invention.

FIGS. 5 and 6 show an example of a fluid dispensing system 400 according to the present invention. The geometry and mechanism of the system 400 is variable depending on the operation of the fluid dispensing cartridge selected for use with the system 400. As best seen in FIG. 5, the system 400 optionally includes a mounting assembly 410 having a plurality of stations 420 at which a fluid dispensing cartridge 10,320 in accordance with the present invention may be mounted. The stations 420 preferably include mounting apertures 430 selectively positioning a plurality of fluid dispensing cartridges 10,320 adjacent to an actuator assembly 40.

The fluid dispensing system 400 also optionally includes a receiving assembly 440 retaining a plurality of receiving members 450. The receiving members 450 maybe any item on which it is desired to dispense fluids from cartridges 10,320. Examples of suitable receiving members 450 are slides, trays and mixing baths. In a preferred embodiment, the receiving members 450 are microscope slides having substrates positioned on them. Examples of suitable substrates are thin slices of tissue samples. Optionally, receiving members 450 may be mounted on spring loaded heating pads 460 providing selective heating of the slides.

Generally speaking, the receiving assembly 440 is positioned generally beneath mounting assembly 410 taking advantage of gravity to deliver fluids dispensed from cartridges 10,320. Preferably, the mounting assembly 410 and receiving assembly 440 are movable with respect to one another so that plural cartridges 10,320 can be positioned to dispense fluids on any desired receiving member 450. Any combination of movability of the mounting assembly 410 and the receiving assembly 440 may be selected. For example, both may be movable or only one may be movable and the other stationary. As shown in FIG. 6, the receiving members 450 may all be the same type of items, such as slides or alternatively may include different types of items such as slides and containers. Preferably, the mounting assembly 410 is a carousel that is rotatable about a central axis.

In one example of operation of the dispensing system 400, the mounting assembly 410 is rotated so that individual cartridges 10,320 are selectively positioned adjacent actuator assembly 40. Alternatively, an actuator assembly 40 may be positioned adjacent to each cartridge 10,320 such that rotation of the mounting assembly 410 is not required. The actuator assembly 40 can be any activation device that triggers the cartridge 10,320 to emit a controlled amount of fluid.

Preferably, the mounting assembly may be both translated and rotated with respect to the receiving assembly 440 so that an individual cartridge 10,320 can be selectively positioned above any receiving member 450. Once the cartridge 10,320 is positioned above a receiving member 450, actuator assembly 40 triggers the cartridge 10,320 to emit a controlled amount of fluid onto the receiving member 450.

As seen in FIGS. 5 and 6, in a preferred embodiment the mounting assembly 410 is rotatably attached to a support member 470 such that the cartridges 10,320 can be rotated with respect to the actuator assembly 40. Actuator assembly 40 is fixedly attached to the support member 470, optionally beneath mounting assembly 410. Preferably, support member 470 can be translated horizontally such that the cartridges 10,320 can be both rotated and translated with respect to the receiving members 450. In this manner, a chosen cartridge 10,320 can be selectively positioned above any receiving member 450.

As seen in the illustrated embodiment, the actuator assembly 40 may optionally include three actuators 480,490,500 used to dispense fluid onto three rows 510,520,530 of receiving members, respectively. In operation, actuator 480 is adapted to dispense fluids onto receiving members 450 in row 510, actuator 490 is adapted to dispense fluids onto receiving members 450 in row 520 and actuator 500 is adapted to dispense fluids onto receiving members 450 in row 530. Of course, as will be understood by those of skill in the art, any number of actuators and/or receiving members can be employed without departing from the scope of the present invention.

As shown in FIG. 5, the system 400 optionally includes supply containers 550, drain containers 560 and valves 570. Supply containers 550 can be used to hold liquids such as water for rinsing receiving members 450. Valves 570 preferably include switches for directing the flow of liquids when rinsing the receiving members 450. In addition, the valves 570 are used to direct the flow of liquids into drain containers 560 after the liquids have been used to rinse receiving members 450.

Turning now to the structure of cartridges 10,320, it is preferred that a horizontal cross-sectional shape of the cartridges 10,320 lacks symmetry. In this way, a mounting aperture 430 in mounting assembly 410 is similarly shaped requiring insertion to be in a particular desired orientation. For example, a substantially trapezoidal shape maybe selected promoting the desired placement orientations. FIGS. 7 and 8 show examples of cartridges 10,320 having substantially trapezoidal cross-sections. These cartridges are adapted to fit within substantially trapezoidal mounting apertures 430 (as shown in FIG. 6). In other embodiments, the mounting apertures 430 and cartridges 10,320 are other similarly oriented shapes that lack symmetry.

Optionally a mounting mechanism can be utilized to releasably attach a cartridge 10,320 within a corresponding mounting aperture 430 of mounting assembly 410. In one example, as shown in FIGS. 1-3 and 7, a ball detent seat 580 is provided on an exterior surface of cartridge 10. As seen in FIG. 6, corresponding balls 590, optionally spring loaded, are situated on the mounting assembly 410 adjacent each mounting aperture 430. Before insertion into a mounting aperture 430, the cartridge 10 must be properly aligned such that the trapezoidal shape of cartridge 10 is in vertical alignment with the corresponding trapezoidal mounting aperture 430. For proper insertion, the cartridge 10 must be pushed downward with sufficient force so that the ball 590 slides over a step 600 into position within seat 580. Further downward movement of cartridge 10 is prevented by ledge 610.

In another example, as seen in FIGS. 4 and 8, a vertical ball detent slot 620 is provided on an exterior surface of cartridge 320. Slot 620 provides a guide for the ball 590 as cartridge 320 is inserted into a mounting aperture 430. A ball detent step 630 and ball detent seat 640 also may be provided to promote locking. For proper insertion, the ball 590 is put into vertical alignment with slot 620 and the cartridge 320 is pushed downward with sufficient force so that the ball 590 slides over step 630 into a position within seat 640. Further downward movement of cartridge 320 is prevented by ledge 650.

Figure 9:
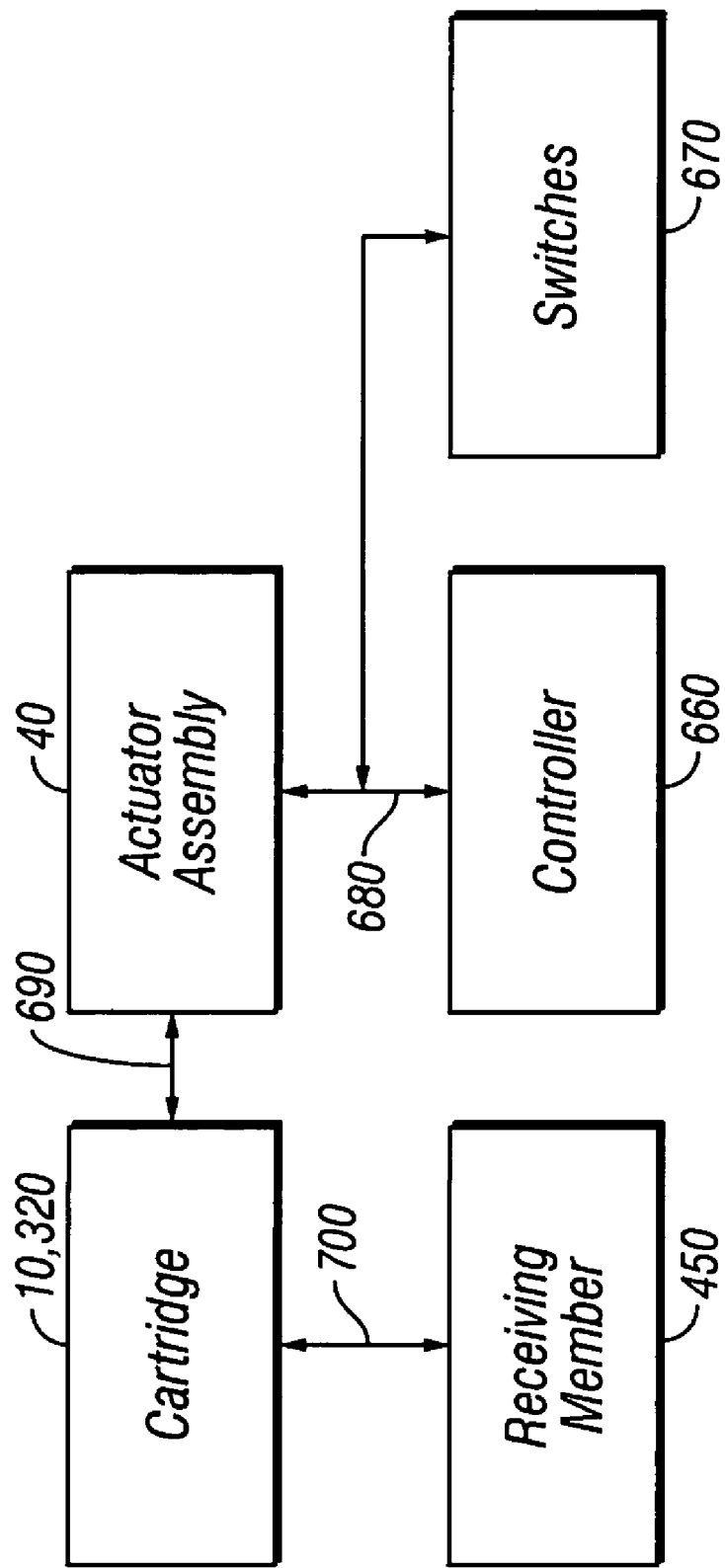
FIG. 9 is a flowchart of an embodiment of an assembly in accordance with the present invention.

With reference to FIG. 9, the actuator assembly 40 is preferably activated using a controller 660 including switches 670. Optionally the controller 660 is a programmable computer having a wireless communication link 680 with actuator assembly 40. Alternatively, controller 660 is anything that causes the actuator assembly 40 to be activated and may include a wire communication link and/or a wireless communication link. Once activated, the actuator assembly 40 utilizes a magnetic link 690 to cause fluid dispenser 30 to dispense fluid 700 onto a receiving member 450.

Thus, it is seen that a fluid dispensing reagent cartridge is provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A fluid dispensing system comprising:
   a linearly translatable mounting assembly having a plurality of fluid dispensing cartridge mounting stations;
   a receiving assembly positioned beneath the mounting assembly, the receiving assembly including a plurality of receiving member positions on its top surface;
   a plurality of heating elements respective ones of which are situated beneath the plurality of receiving member positions; and
   a plurality of self-contained fluid dispensing cartridges individually mounted at respective fluid dispensing mounting stations, wherein each fluid dispensing cartridge comprises a fluid reservoir releasably coupled to a fluid dispensing assembly, the fluid reservoir defined by a cover comprising an open end in fluid communication with the fluid dispensing assembly and a side opposite the open end, wherein the reservoir provides a fluid source.

2. The fluid dispensing system of claim 1 wherein the translatable mounting assembly also is rotatable about an axis of rotation that is linearly translatable.

3. The fluid dispensing system of claim 2 wherein each of said mounting stations further comprises a retaining assembly at each of said fluid dispensing cartridge mounting stations, the retaining assembly including a spring loaded ball disposed adjacent a mounting aperture and each of said fluid dispensing cartridges include a matching ball detent set disposed on an exterior surface of the cartridge.

4. The fluid dispensing system of claim 1 wherein each of the mounting stations includes an aperture or indentation shaped to match a corresponding horizontal cross-sectional shape of the corresponding fluid dispensing cartridge.

5. The fluid dispensing system of claim 1 further including at least one receiving member at a respective one of said receiving member positions.

6. The fluid dispensing system of claim 5 wherein the receiving member is a tray.

7. The fluid dispensing system of claim 5 wherein the receiving member is a tray having a microscope slide mounted thereon.

8. The fluid dispensing system of claim 5 wherein each of said at least one tray includes a structure adapted to receive a microscope slide.

9. The fluid dispensing system of claim 5 wherein each of said at least one tray includes a fluid receiving surface.

10. The fluid dispensing system of claim 5 wherein each of said at least one tray includes a fluid receiving surface wherein a respective one of the fluid dispensing cartridge mounting stations is positionable above the fluid receiving surface by linear translation of the mounting assembly.

11. The fluid dispensing system of claim 5 wherein each of said at least one tray includes a fluid receiving surface wherein a respective one of the fluid dispensing cartridge mounting stations is positionable above the fluid receiving surface by one or both of linear translation and rotation of the mounting assembly.

12. The fluid dispensing system of claim 1 further comprising a plurality of receiving members each situated at a respective one of said receiving member positions.

13. The fluid dispensing system of claim 12 wherein each of said receiving members is a tray.

14. The fluid dispensing system of claim 1 wherein said receiving member positions are linearly arranged on a surface of the receiving assembly.

15. The fluid dispensing system of claim 1 wherein said receiving member positions are arranged in at least two rows on a surface of the receiving assembly, and the mounting assembly being linearly translatable above said rows.

16. The fluid dispensing system of claim 1 further comprising a support member upon which said mounting assembly is translatably mounted.

17. The fluid dispensing system of claim 1 further comprising a support member upon which said mounting assembly is translatably and rotatably mounted.

18. The fluid dispensing system of claim 1 wherein said receiving assembly is stationary.

19. The fluid dispensing system of claim 1 wherein the heating elements are selectively controlled for heating different receiving members.

20. The fluid dispensing system of claim 1 wherein said heating elements include spring loaded heating pads.

21. The fluid dispensing system of claim 1 further comprising at least one fluid supply container location below said top surface of said receiving assembly.

22. The fluid dispensing system of claim 21 further comprising at least one valve positioned between each of said at least one fluid supply container location and said top surface.

23. The fluid dispensing system of claim 22 further comprising at least one fluid supply container positioned at one of said at least one fluid supply container locations.

24. The fluid dispensing system of claim 1 further comprising at least one drain container positioned below said top surface of said receiving assembly.

25. The fluid dispensing system of claim 24 further comprising at least one valve positioned between each of said at least one drain container and said top surface.

26. The fluid dispensing system of claim 25 further comprising at least one drain container positioned at one of said at least one drain container locations.

27. The fluid dispensing system of claim 1 further comprising:

at least one fluid supply container location below said top surface of said receiving assembly; and at least one drain container location below said top surface of said receiving assembly.

28. The fluid dispensing system of claim 27 further comprising at least one valve positioned between each of said at least one fluid supply container locations and said top surface and between each of said at least one drain container locations and said top surface.

29. The fluid dispensing system of claim 1 wherein each of said mounting stations further comprises a retaining assembly at each of said fluid dispensing cartridge mounting stations.

30. The fluid dispensing system of claim 1 wherein the cover comprises a valve.

31. A fluid dispensing system comprising:

a receiving assembly including a top surface and a plurality of receiving member positions on the top surface;

a plurality of heating elements respective ones of which are situated beneath the plurality of receiving member positions;

a linearly translatable mounting assembly having a plurality of fluid dispensing cartridge mounting stations thereon;

a plurality of self-contained fluid dispensing cartridges mounted to the mounting assembly at the mounting stations, wherein each fluid dispensing cartridge includes a fluid reservoir releasably coupled to a fluid dispensing assembly, the fluid reservoir defined by a cover comprising an open end in fluid communication with the fluid dispensing assembly and a side opposite the open end, wherein the reservoir provides a fluid source;

a plurality of actuator assemblies, at least one of which corresponds to each of the fluid dispensing cartridge mounting stations; and a controller in communication with each of the actuator assemblies, the controller actuating the actuator assemblies to dispense fluid from cartridges mounted in the respective cartridge mounting stations.

32. A fluid dispensing system comprising:

a movable mounting assembly having a plurality of fluid dispensing cartridge mounting stations;

a substantially stationary receiving assembly positioned beneath the mounting assembly, the receiving assembly including a plurality of receiving member positions on its top surface and heating elements situated beneath the plurality of receiving member positions; and a plurality of self-contained fluid dispensing cartridges individually mounted on respective fluid dispensing mounting stations wherein each fluid dispensing cartridge comprises a fluid reservoir releasably coupled to a fluid dispensing assembly, the fluid reservoir defined by a cover comprising an open end in fluid communication with the fluid dispensing assembly and a side opposite the open end, wherein the reservoir provides a fluid source.

33. A method of dispensing fluids on to samples mounted on microscope slides comprising:

positioning a plurality of microscope slides one each on a respective tray;

positioning each of said trays on a receiving assembly in a linear arrangement, the receiving assembly comprising heating elements situated in a linear arrangement beneath each of said trays;

mounting a self-contained fluid dispensing cartridge on a linearly and rotatably translatable mounting assembly, wherein the fluid dispensing cartridge includes a reservoir releasably coupled to a fluid dispensing assembly, the reservoir defined by a cover comprising an open end in fluid communication with the fluid dispensing assembly and a side opposite the open end, wherein the reservoir provides a fluid source;

linearly and rotatably moving said mounting assembly to position the fluid dispensing cartridge above a selected one of said trays; and dispensing fluid.

34. The method of claim 33 wherein dispensing fluid comprises operating an actuator assembly.

35. The method of claim 33 wherein plural microscope slides are positioned on a respective tray.

* * * * *